United States Patent
Gozani

[19]

[11] Patent Number: 5,976,094
[45] Date of Patent: Nov. 2, 1999

[54] APPARATUS AND METHODS FOR ASSESSMENT OF NEUROMUSCULAR FUNCTION

[75] Inventor: Shai N. Gozani, Brookline, Mass.

[73] Assignee: NeuroMetrix, Inc., Cambridge, Mass.

[21] Appl. No.: 09/022,990

[22] Filed: Feb. 12, 1998

Related U.S. Application Data

[62] Division of application No. 08/886,861, Jul. 1, 1997, Pat. No. 5,851,191.

[51] Int. Cl.$^6$ .................................................... A61B 5/05
[52] U.S. Cl. ............................................................. 600/483
[58] Field of Search .................................. 600/483, 545, 600/546; 128/905

[56] References Cited

U.S. PATENT DOCUMENTS

| | | | |
|---|---|---|---|
| 3,572,322 | 3/1971 | Wade | 600/483 |
| 3,886,931 | 6/1975 | Rodler | 128/2.1 R |
| 4,807,643 | 2/1989 | Rosier | 128/741 |
| 4,811,742 | 3/1989 | Hassel et al. | 128/905 |
| 5,050,612 | 9/1991 | Matsumura | 128/670 |
| 5,080,099 | 1/1992 | Way et al. | 128/640 |
| 5,092,344 | 3/1992 | Lee | 128/741 |
| 5,099,844 | 3/1992 | Faupel | 128/653.1 |
| 5,131,401 | 7/1992 | Westenskow et al. | 128/741 |
| 5,143,081 | 9/1992 | Young et al. | 128/741 |
| 5,203,330 | 4/1993 | Schaefer et al. | 128/640 |
| 5,215,100 | 6/1993 | Spitz et al. | 128/741 |
| 5,255,677 | 10/1993 | Schaefer et al. | 128/640 |
| 5,327,902 | 7/1994 | Lemmen | 128/734 |
| 5,333,618 | 8/1994 | Lekhtman et al. | 128/734 |
| 5,379,764 | 1/1995 | Barnes et al. | 128/633 |
| 5,466,256 | 11/1995 | McAdams et al. | 607/142 |
| 5,467,768 | 11/1995 | Suda et al. | 128/640 |
| 5,496,363 | 3/1996 | Burgio et al. | 607/152 |
| 5,511,553 | 4/1996 | Segalowitz | 128/696 |
| 5,540,235 | 7/1996 | Wilson | 600/564 |
| 5,560,372 | 10/1996 | Cory | 128/741 |

FOREIGN PATENT DOCUMENTS

| | | |
|---|---|---|
| 0 025 222 A2 | 3/1981 | European Pat. Off. . |
| 0 436 121 A1 | 7/1991 | European Pat. Off. . |
| WO 91/16001 | 10/1991 | WIPO . |
| WO 92/03974 | 3/1992 | WIPO . |

OTHER PUBLICATIONS

Testerman, Roy, "Method of Measuring Blood Glucose Level by Sensing Evoked Action Potentials in Peripheral Nerve," Research Disclosure, 227:92, Article No. 22728 (Mar. 1983).

Oh, Shin J., M.D., "Clinical Electromyography: Nerve Conduction Studies," (Williams & Wilkins, 2nd Ed., 1993).

Gilliatt, R.W. and Willison, R.G., "Refractory and Supernormal Periods of the Human Median Nerve," (*J. Neurol. Neurosurg. Psychiat.*, 2:1963), pp. 136–147.

Lindstrom, P. and Brismar, T., "Mechanism of Anoxic Conduction Block in Mammalian Nerve," (*Acta Physiol Scand*, 141:1991), pp. 429–433.

(List continued on next page.)

*Primary Examiner*—William E. Kamm
*Attorney, Agent, or Firm*—Testa, Hurwitz & Thibeault, LLP

[57] ABSTRACT

Apparatus and methods are provided for the assessment of neuromuscular function. Using an apparatus of the invention, stimuli are applied to a nerve that traverses the wrist of an individual. The stimuli are applied at a point that is proximal to the wrist. Stimulation of the nerve causes a muscle innervated by that nerve to respond. The muscle response generates a myoelectric potential, which is detected by an apparatus of the invention at a point that is proximal to the wrist. The delay between stimulation of a nerve and detection of a muscular response to that stimulation is processed to indicate an assessment of neuromuscular function. For example, a sufficient delay between application of stimulus and muscle response may indicate the presence of Carpal Tunnel Syndrome.

12 Claims, 8 Drawing Sheets

OTHER PUBLICATIONS

Basmajian, John V. M.D., and De Luca, Carlo J., Ph.D., "Muscles Alive: Their Functions Revealed by Electromyography," (*Williams & Wilkins,* 5th Ed., 1995).

Fujisawa, M., D.D.S. et al., "Surface Electromyographic Electrode Pair With Built–In Buffer–Amplifiers," (*The Journal of Prosthetic Denistry,* vol. 63, No. 3, Mar. 1990), pp. 350–352.

Seneviratne, K.N. and Peiris, O.A., "The Effect of Ischaemia on the Excitability of Human Sensory Nerve," (*J. Neurol. Neurosurg. Psychiat.,* 31:1968), pp. 338–347.

Shefner, Jeremy, M. M.D., "The Use of Sensory Action Potentials in the Diagnosis of Periheral Nerve Disease," (Arch Neurol—vol. 47, Mar. 1990); pp. 341–348.

Brodie, Chaya and Sampson, S.R., "Contribution of Electrogenic Sodium–Potassium ATPase to Resting Membrane Potential of Cultured Rat Skeletal Myotubes," (*Brain Research,* 347:1985), pp. 28–35.

Stewart, Mark A., et al., "Substrate Changes in Peripheral Nerve During Ischemia and Wallerian Degeneration," (*Journal of Neurochemistry,* vol. 12, 1965), pp. 719–727.

Bostock, H., et al., "Changes in Excitability and Accommodation of Human Motor Axons Following Brief Periods of Ischaemia," (*Journal of Physiology,* 441:1991 Great Britain), pp. 513–535.

Nishimura, Suzushi, et al., "Clinial Application of an Active Electrode Using an Operational Amplifier," (*IEEE Transactions on Biomedical Engineering,* vol. 39, No. 10, Oct. 1992), pp. 1096–1099.

http://www.aosi.com/neumed/overview.html.

http://www/cs.msstate.edu/~csmith/biomech/nrve-cond.html.

http://www.asoi.com/neumed/p.html.

http://www.netspace.org/~simon/Pictures.html1#NCV.

"Now Diagnose and Monitor the Clinical Progress of Compression Neuropathies Such as Carpal Tunnel Syndrome——in the Office or Clinic", *Neuroton Medical,* Lawrenceville NJ (product Literature)(1991).

APPARATUS AND METHODS FOR ASSESSMENT OF NEUROMUSCULAR FUNCTION

This is a divisional of application Ser. No. 08/886,861 filed on Jul. 1, 1997 and now U.S. Pat. No. 5,851,191.

FIELD OF THE INVENTION

The invention relates to apparatus and methods for assessment of neuromuscular function. More specifically, the invention relates to apparatus and methods for diagnosing peripheral nerve and muscle pathologies based on assessments of neuromuscular function.

BACKGROUND OF THE INVENTION

There are many clinical and non-clinical situations that call for a rapid, reliable and low-cost assessments of neuromuscular function. Reliable and automated devices are needed to monitor neuromuscular function in surgical and intensive care settings. For example, muscle relaxants significantly improve surgical procedures and post-operative care by regulating the efficacy of nerve to muscle coupling through a process called neuromuscular blockade. They are, however, difficult to use in a safe and effective manner because of the wide variation and lack of predictability of patient responses to them. In another setting, an easy to use and reliable indicator would be beneficial in assessing potential contamination exposure situations by chemical agents. These agents disrupt neuromuscular function and effectively cause neuromuscular blockade, putting soldiers and civilians at risk.

The most common causes of neuromuscular disruption are, however, related to pathologies of the peripheral nerves and muscles. Neuromuscular disorders, such as, for example, Carpal Tunnel Syndrome (CTS), are very common and well known to the general public. Despite their extensive impact on individuals and the health care system, detection and monitoring of such neuromuscular pathologies remains expensive, complicated, and highly underutilized.

CTS is one of the most common forms of neuromuscular disease. The disease is thought to arise from compression of the Median nerve as it traverses the wrist. CTS often causes discomfort or loss of sensation in the hand, and, in severe cases, a nearly complete inability to use one's hands. Highly repetitive wrist movements, as well as certain medical conditions, such as, for example, diabetes, rheumatoid arthritis, thyroid disease, and pregnancy, are thought to be factors that contribute to the onset of CTS. In 1995, the US National Center for Health Statistics estimated that there were over 1.89 million cases of CTS in the United States alone.

Effective prevention of CTS requires early detection and subsequent action. Unfortunately, the state of CTS diagnosis is rather poor. Even experienced physicians find it difficult to diagnose and stage the severity of CTS based on symptoms alone. The only objective way to detect CTS is to measure the transmission of neural signals across the wrist. The gold standard approach is a formal nerve conduction study by a clinical neurologist, but this clinical procedure has a number of important disadvantages. First, it is a time consuming process that requires the services of a medical expert, such as a neurologist. Second, the procedure is very costly (e.g., $600–$1000). Furthermore, it is not available in environments where early detection could significantly decrease the rate of CTS, such as the workplace where a significant number of causes of CTS appear. As a result of these disadvantages, formal electrophysiological evaluation of suspected CTS is used relatively infrequently, which decreases the likelihood of early detection and prevention.

The prior art reveals a number of attempts to simplify the assessment of neuromuscular function, such as in diagnosing CTS, and to make such diagnostic measurements available to non-experts. Rosier (U.S. Pat. No. 4,807,643) describes a portable device for measuring nerve conduction velocity in patients. This instrument has, however, several very important disadvantages. First, it requires placement of two sets of electrodes: one set at the stimulation site and one set at the detection site. Consequently, a skilled operator with a fairly sophisticated knowledge of nerve and muscle anatomy must ensure correct application of the device. Inappropriate placement of one or both of the electrode sets can lead to significant diagnostic errors. Second, the Rosier apparatus suffers from the disadvantage that it is not automated. In particular, it demands that the user of the device establish the magnitude of the electrical stimulus, as well as a response detection threshold. These parameters are difficult to determine a priori, and their rapid and correct establishment requires an advanced understanding of both neurophysiology and the detailed electronic operation of the apparatus.

Spitz, et al. (U.S. Pat. No. 5,215,100) and Lemmen (U.S. Pat. No. 5,327,902) have also attempted to enhance the earlier prior art: Specifically, they proposed systems that measure nerve conduction parameters between the arm or forearm and the hand, such as would be required for diagnosing CTS. In both cases, however, electrode supporting structures or fixtures were proposed that would substantially fix the positions at which the stimulation electrodes contact the arm and the detection electrodes contact the hand. Furthermore, these systems suffer, from several important disadvantages. First, both systems are rather large and bulky, because they include a supporting fixture for the arm and hand of an adult. This severely limits their portability and increases their cost. Second, these devices still require highly trained operators who can make the appropriate adjustments on the apparatus so as to insure electrode contact with the proper anatomical sites on the arm and hand. A third disadvantage of both systems is that they continue to demand multiple operator decisions regarding stimulation and detection parameters. Finally, these prior art systems suffer from the disadvantage that they do not automatically implement the diagnostic procedure and indicate the results in a simple and readily interpretable form.

There remains a need, therefore, for apparatus and methods for assessing neuromuscular function that are less time consuming, less expensive, and more available to a wider range of the general public (i.e., are more portable and easy to use). Such apparatus and methods are needed to provide more widespread early detection and prevention of neuromuscular pathologies, such as CTS. The present invention addresses these needs.

SUMMARY OF THE INVENTION

In accordance with the invention, apparatus and methods are provided for the substantially automated, rapid, and efficient assessment of neuromuscular function without the involvement of highly trained personnel. Assessment of neuromuscular function occurs by stimulating a nerve, then measuring the response of a muscle innervated by that nerve. The muscle response is detected by measuring the myoelectric potential generated by the muscle in response to the stimulus. One indication of the physiological state of the nerve is provided by the delay between application of a stimulus and detection of a muscular response. If the nerve is damaged, conduction of the signal via the nerve to the muscle, and, hence, detection of the muscle's response, will be slower than in a healthy nerve. An abnormally high delay between stimulus application and detection of muscle response indicates, therefore, impaired neuromuscular function. In apparatus and methods of the invention, both the application of stimulus and the detection of responses is carried out entirely at a position that is immediately proximal to the wrist of an individual (i.e., the wrist crease). This anatomical location is familiar and easy to locate, thus ensuring correct placement of the apparatus at the assessment site by non-experts while still maintaining the accuracy of results. This ease of use increases the availability and decreases the cost of diagnosing pathologies such as Carpal Tunnel Syndrome (CTS).

Apparatus and methods of the invention assess neuromuscular function in the arm of an individual by using a stimulator to apply a stimulus to a nerve that traverses the wrist of the individual. The stimulator is adapted for applying the stimulus to the nerve at a position which is proximal to the wrist of the individual. The stimulus may be, for example, an electrical stimulus or a magnetic stimulus. Other types of stimuli may be used. A detector, adapted for detecting the myoelectric potential generated by a muscle in response to the stimulus, detects the response of the muscle to the stimulus at a site that is also proximal to the wrist of the individual. A controller then evaluates the physiological function of the nerve by, for example, determining a delay between application of stimulus and detection of myoelectric potential. The delay is then correlated to the presence or absence of a neuromuscular pathology, such as, for example, Carpal Tunnel Syndrome (CTS).

In a preferred embodiment, the stimulator and the detector are both in electrical communication with electrodes adapted for placement on the arm of an individual proximal to the wrist. The controller may also be in electrical communication with a reference electrode and a temperature sensor. An apparatus of the invention may further comprise a communications port for establishing communication between the apparatus and an external device, such as, for example, a personal computer.

In another embodiment, an apparatus of the invention further comprises an indicator. The indicator is in electrical communication with the controller and is adapted for indicating the physiological function evaluated by the controller in response to the stimulus applied and myoelectric potential detected. The indicator may comprise a light emitting diode. In a particularly preferred embodiment, the indicator is adapted for indicating the presence or absence of CTS.

An apparatus of the invention may be further embodied in an electrode configuration contained in an electrode housing for releasably securing to the wrist of an individual. The electrode housing contains an attachment mechanism, such as, for example, a non-irritating adhesive material, for securing to the arm of the individual and may be disposable. The electrode housing preferably has a connector for electrical communication with an apparatus comprising a stimulator, a detector, and a processor, as described above.

The electrode housing comprises stimulation and detection electrodes. The stimulation and detection electrodes are sized and shaped in the housing so that they contact an anterior aspect of an arm of the individual proximal to the wrist, when the housing is secured to the wrist of the individual. The electrode configuration may further contain a temperature sensor and/or a reference electrode.

In a preferred embodiment, the electrode configuration comprises a second stimulation electrode and a second detection electrode. The two stimulation electrodes are positioned substantially in the center of the electrode housing and are arranged so that they are positioned at opposite ends of the housing. The two stimulation electrodes are preferably arranged so that, when the housing is placed on the anterior aspect of an arm of a user, one of the stimulation electrodes is located immediately proximal to the wrist and the other at a location more proximal from the wrist. The two detection electrodes are also located at opposite ends of the housing, but they are positioned such that, when placed on the anterior aspect of an arm of a user, one detection electrode is located on the medial, and the other on the lateral, side of the wrist.

Methods of the invention relate to the assessment of neuromuscular function using an apparatus of the invention. Using an apparatus, as described above, a stimulus is applied to a nerve that traverses the wrist of an individual proximal to the wrist. A muscle innervated by the nerve responds and thereby generates a myoelectric potential, which is detected proximal to the wrist of the individual. The detected response is processed by determining a first derivative of the myoelectric potential and, preferably, a second derivative of the myoelectric potential. In a preferred embodiment, these derivatives are used to determine an appropriate stimulation level, as well as to determine the delay between application of stimuli and detection of the associated responses. In another embodiment, additional measurements related to the delay are taken. For example, changes in the delay induced by application of at least two stimulus applications is determined. The delay and associated parameters calculated from any of the measurements are then correlated to a physiological function of the nerve and muscle.

In preferred embodiments, an apparatus of the invention is used to indicate the presence or absence of CTS. A plurality of stimuli are applied to a nerve passing through the carpal tunnel, such as, for example, the Median nerve. The stimuli may be delivered one at a time at a predetermined rate or they may be delivered in pairs at a predetermined rate. If delivered in pairs, the application of stimuli is separated by a predetermined time interval.

A plurality of myoelectric potentials are generated by a muscle innervated by the stimulated nerve in response to the stimuli. Each myoelectric potential is generated in response to a respective stimulus application. A delay for each of said stimulus applications and detected responses is determined. Statistics such as, for example, mean and standard deviation, are calculated for the plurality of delays. The probable value that the individual has CTS is calculated based on these statistics. An indication of the presence or absence of CTS is then given based on that value.

In other embodiments of the invention, the method may involve further steps. For example, in one embodiment of the invention, the method relates to calculating the difference between delays measured in response to two stimuli delivered at short temporal intervals, and determining the probable value that an individual has CTS based on these delay differences and calculated statistics, as described above. In another embodiment, a level of noise is measured prior to stimulating the nerve. In yet another embodiment, the mean and standard deviation of the delays is adjusted relative to the skin temperature.

An apparatus and method for the essentially automated and accurate assessment of neuromuscular function is therefore provided. The apparatus and methods of the invention allow for the less costly and more readily available detection of neuromuscular pathologies, such as, for example, CTS, without the aid of a skilled professional.

The invention will be understood further upon consideration of the following drawings, description, and claims.

DETAILED DESCRIPTION OF THE INVENTION

Figure 1:
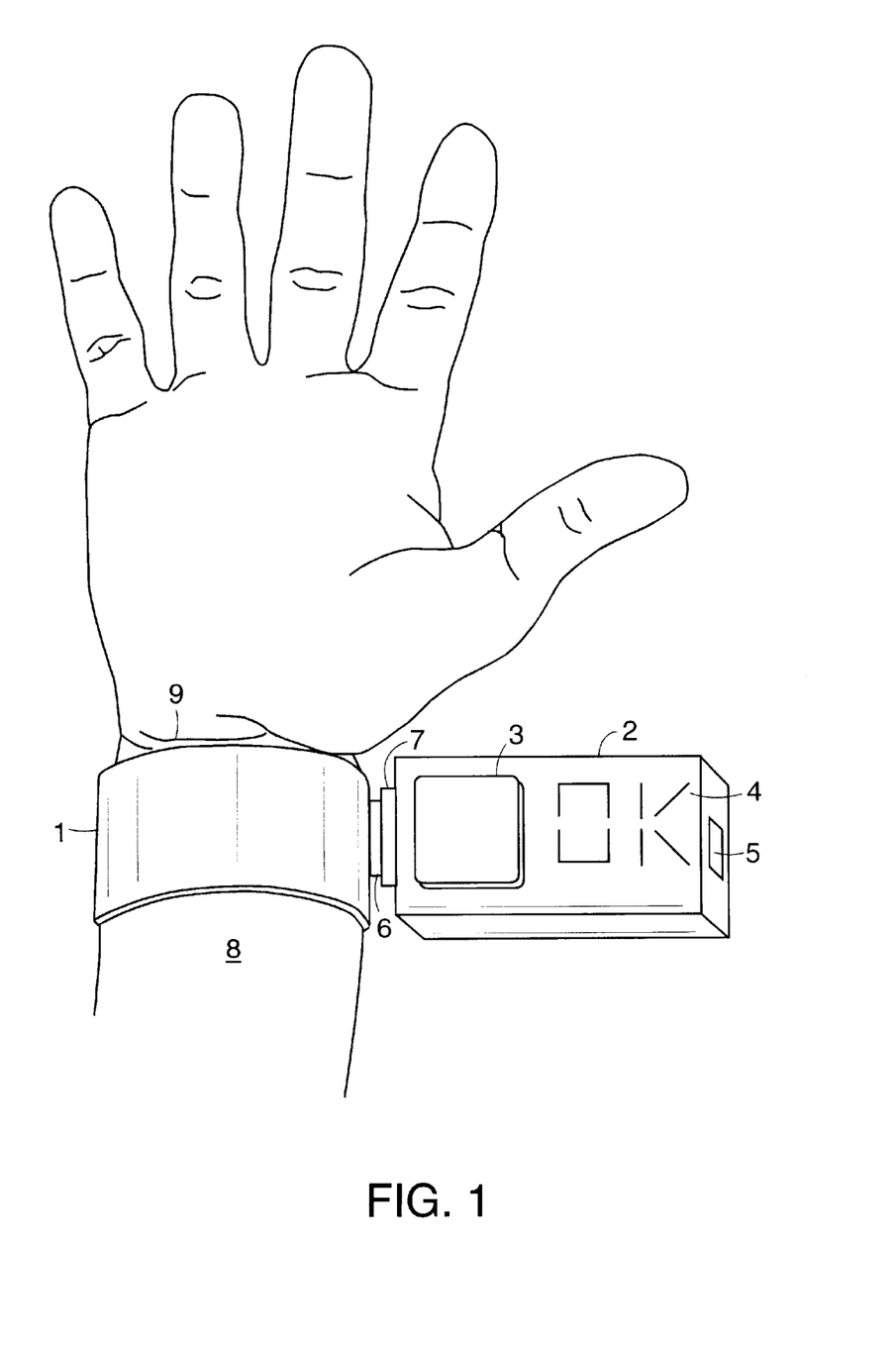
FIG. 1 is an illustration of an embodiment of the apparatus of the invention attached to the wrist of a user.

An illustrative embodiment of an apparatus of the invention and its placement on the users forearm 8 is shown in FIG. 1. The invention consists of two major components: a neuromuscular electrode 1 and an electronic monitor 2. The neuromuscular electrode I includes both a stimulator and a detector. The electronic monitor 2 includes both a controller and an indicator. In this embodiment, the neuromuscular electrode 1 and electronic monitor 2 are physically separable with electrical connections between the two components established by physical contact between a connector 6, associated with the neuromuscular electrode 1 and connector slot 7 associated with the electronic monitor 2. In another embodiment, neuromuscular electrode 1 and electronic monitor 2 constitute a single, physically inseparable unit. The electronic monitor 2 contains means to actuate the diagnostic process. Referring to the illustrative embodiment shown in FIG. 1, a push-button 3 is provided to initiate said diagnostic process. The electronic monitor 2 also contains an indicator to display or convey the results of the diagnostic process. Referring to the illustrative embodiment shown in FIG. 1, an indicator includes a display 4, which includes two multi-segment light-emitting diodes (LEDs) and which provides feedback and results. Other indicators may be used, including, but not limited to, single and multicolor discrete LEDs. Other types of indicators, such as, for example, speakers, may provide auditory signals. The electronic monitor 2 also contains a communications port to connect and communicate with external devices. Referring to the illustrative embodiment shown in FIG. 1, the communications port includes a jack 5 into which a cable may be inserted. The other end of the cable is then connected to any number of different devices, including, but not limited to, computers and telephone lines.

Figure 2A:
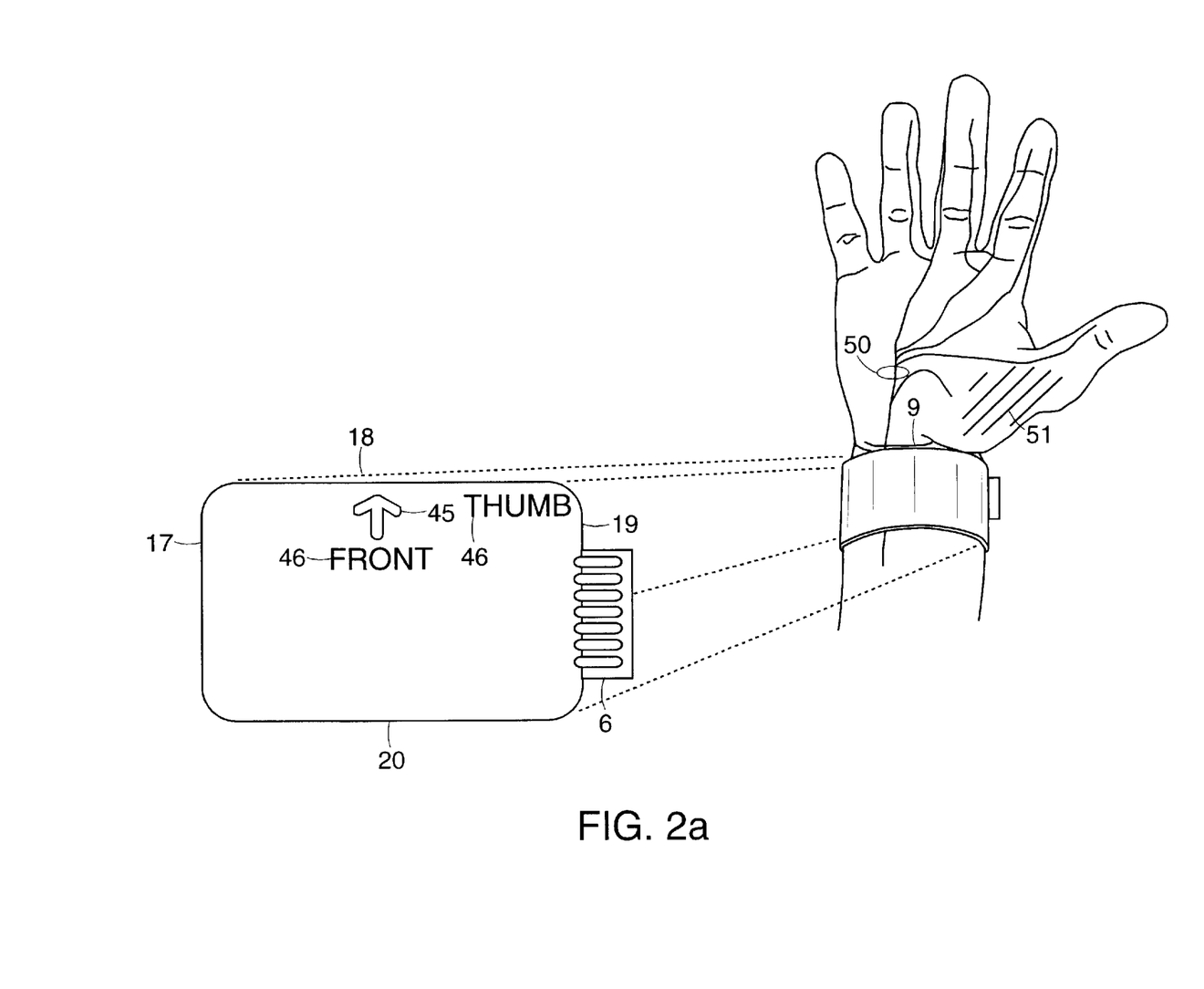
FIG. 2A shows a top surface of the embodiment of the apparatus of the invention shown in FIG. 1.
Figure 2B:
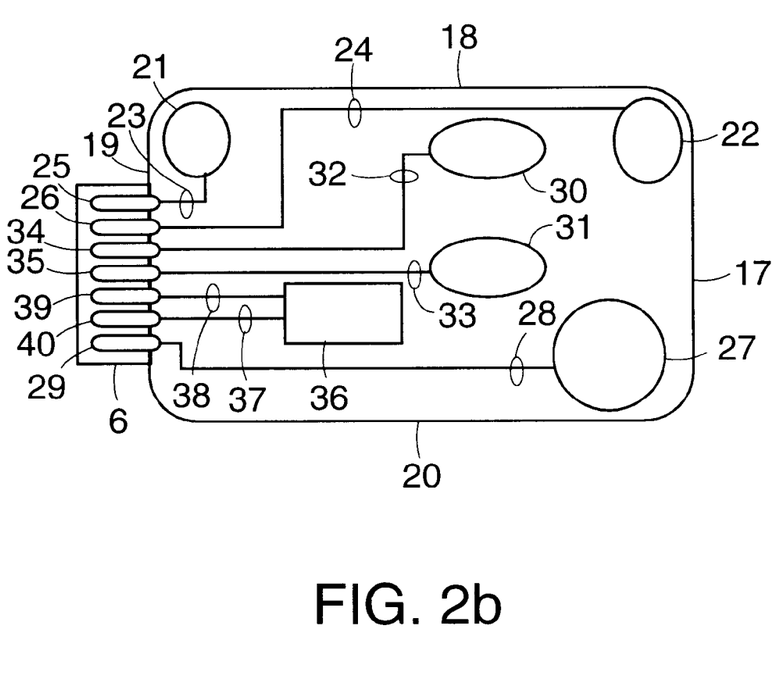
FIG. 2B illustrates a bottom surface of the embodiment of the apparatus of the invention shown in FIG. 1 depicting an electrode configuration.

The neuromuscular electrode 1 delivers electrical stimuli to the skin surface, detects biopotentials from the skin surface and measures additional physiological and biological parameters, such as, for example, skin temperature. As shown in FIG. 1, the neuromuscular electrode 1 is placed on the anterior aspect of the forearm 8 immediately proximal to the wrist crease 9. In the preferred embodiment, the physical dimensions of the neuromuscular electrode 1 are chosen from a predetermined set of dimensions which are optimized for the range of wrist sizes found in adults. For example, the electrodes may be configured in a small, regular and large size. Additional embodiments are contemplated in which the neuromuscular electrode 1 includes means to vary its physical dimensions over a predetermined range such as, for example, being contained in an electrode housing, such as, an adjustable band or strap. The band or strap may also be detachable. An illustrative embodiment of the neuromuscular electrode 1 is shown in FIG. 2A. FIG. 2A shows the top surface of the neuromuscular electrode 1 and its proper location on the user's wrist. In one embodiment, the top surface of the neuromuscular electrode 1 contains printed instructions 46 and/or other visual indications 45 to help the user properly position it. FIG. 2B shows the bottom surface of the neuromuscular electrode 1. The illustrative configuration allows muscle activity in the Thenar muscle group 51 to be evoked and sensed when the neuromuscular electrode 1 is positioned immediately proximal to the wrist crease 9, as shown in FIG. 2A. Two bioelectrical transduction sites, 30 and 31, hereafter referred to as the stimulation sites, are positioned approximately midway between the lateral end 19 and medial end 17 of the neuromuscular electrode 1. The two stimulation sites, 30 and 31, are arranged in a distal to proximal line such that one of the sites is near the distal end 18 of the neuromuscular electrode 1 and one of the sites is near the proximal end 20 of the neuromuscular electrode 1.

The stimulation sites may consist of stimulation electrodes comprised of delineated areas of bioelectrical signal transduction means that convert electronic signals into electrochemical ones and vice versa. In a preferred embodiment, these sites are composed of a plurality of layers of different materials with substantially the same area. A first layer is directly attached to the bottom face of the neuromuscular electrode 1 and is preferably formed by a thin layer of silver. A second layer is attached to first layer and preferably consists of a silver-chloride salt. A third layer is attached to second layer and contacts the user's skin on its exposed surface. The third layer is preferably composed of an electrolyte hydrogel, such as, for example, sodium chloride.

When the neuromuscular electrode 1 is properly positioned as shown in FIG. 2A, the two stimulation sites, 30 and 31, will overlie the Median nerve 50. The nerve 50 is stimulated by passing a low amplitude current (e.g., typically less than 10 milliamps) through the two stimulation sites, 30 and 31. The current is provided by an external source electrically coupled to contacts, 34 and 35, on the external connector 6. The contacts, 34 and 35, and the stimulation sites, 30 and 31, are coupled by electrically conductive and insulated means, 32 and 33.

Two transduction sites, 21 and 22, hereafter referred to as the detection sites, are positioned at the extreme lateral end 19 and medial end 17 of the neuromuscular electrode 1 near its proximal end 18. In a preferred embodiment, the detection sites, 21 and 22, consist of detection electrodes comprised of delineated areas of bioelectrical signal transduction means that convert electronic signals into electrochemical ones and vice versa. In a preferred embodiment, these sites are constructed in a substantially similar manner to the stimulation sites, 30 and 31.

Contraction of the Thenar muscles 51 will generate a myoelectric potential and create a bioelectrical potential difference between the lateral 21 and medial 22 detection sites due to the relative proximity of the lateral detection site 21 to the Thenar muscles 51. This potential difference may be measured as a small (e.g., typically less than 0.5 mV) differential voltage between contacts, 25 and 26, on the external connector 6. The contacts, 25 and 26, and the detection sites, 21 and 22, are coupled by electrically conductive and insulated means, 23 and 24. The measurement of the differential voltage signal is enhanced by the availability of a reference potential, which is provided by transduction site 27, hereafter referred to as the reference site, or reference electrode. This site is positioned along the medial end 17 of the neuromuscular electrode 1 towards its proximal end 20. The position of the reference site 27 is, however, not critical and has relatively little effect on the function of the invention. In a preferred embodiment, the reference site 27 is constructed in a substantially similar manner to the stimulation sites, 30 and 31, and detection sites, 21 and 22. The reference potential is made available at a contact 29 on the external connector 6, which is coupled to the reference site 27 by electrically conductive and insulated means 28.

The neuromuscular electrode 1 contains a temperature sensor 36, such as, for example, a DS 1820 (Dallas Semiconductor, Dallas, Tex.) or a thermistor. The temperature sensitive part of the sensor 36 contacts the users skin directly or indirectly through an intermediary material that efficiently conducts heat. The temperature sensor 36 can be placed at any available location within the area of the neuromuscular electrode 1. The temperature sensor 36 is powered and transmits temperature information to electronic monitor 2 through two or more contacts, 39 and 40, on the external connector 6. The contacts, 39 and 40, and the temperature sensor 36 are coupled by electrically conductive and insulated means, 37 and 38.

Additional configurations and arrangements of transduction sites and sensors have been contemplated and should be considered within the scope of the present invention. One such configuration utilizes a single pair of transduction sites for both stimulation and detection through electronic multiplexing.

The electronic monitor 2 has a number of functions. The monitor 2 detects, amplifies, processes and stores bioelectrical potentials, such as those generated by nerve or muscle activity. It also generates stimuli, such as steps of electrical current, with sufficient magnitude to trigger impulses in nerves or muscles. In addition, it communicates with the user and with external instruments, such as, for example, a personal computer. Finally, the electronic monitor 2 includes a controller to process data and control the intensity and duration of stimulus applications.

Figure 3:
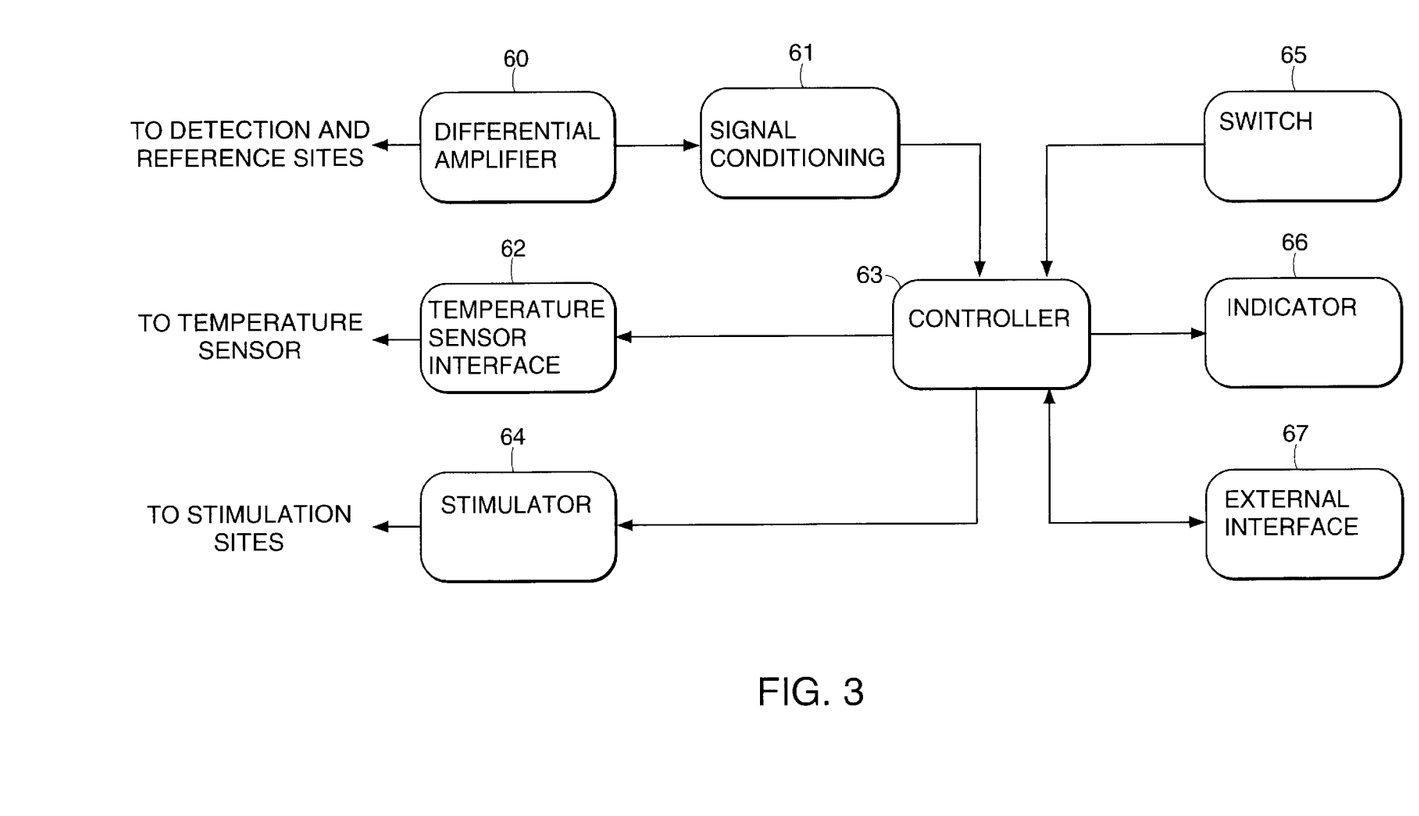
FIG. 3 is a block diagram of an embodiment of the apparatus of the invention.

An illustrative block diagram of the electronic monitor 2 of FIG. 1 is shown in FIG. 3. Differential amplifier 60 amplifies the voltage difference between the input terminals and generates a voltage that is proportional to that voltage difference. When the electronic monitor 2 and neuromuscular electrode 1 of FIG. I are connected by physical contact between connectors, 6 and 7, the differential amplifier 60 of FIG. 3 is electrically coupled to detection sites, 21 and 22, and reference site 27. Since the bioelectrical signals from the body surface typically have a source impedance between about 5 KΩ to about 50 KΩ and contain large common mode signals, the differential amplifier 60 must have a high input impedance, a good common mode rejection ratio and a low leakage current. These requirements are preferably met by an instrumentation amplifier, such as, for example, the INA111 (Burr-Brown, Tuscon, Ariz.) or the AD621 (Analog Devices, Norwood, Mass.).

The differential amplifier 60 is electrically coupled to a signal conditioning unit 61 that prepares the signal for analog-to-digital conversion and subsequent processing. The signal conditioning unit 61 preferably removes DC offsets, amplifies, low-pass filters, and creates a DC bias. The signal conditioning unit 61 is electrically coupled to an analog-to-digital converter on the controller 63.

Temperature sensor interface electronics 62 power the temperature sensor and convert temperature related signals into a form interpretable by controller 63. Stimulator 64 generates an electrical impulse with either or both of the magnitude and duration of the impulse being determined by signals from controller 63.

The stimulator 64 is preferably embodied by a circuit which gates the discharge of a capacitor charged to a high voltage (e.g., 100 volts). The capacitance value (e.g., 1 $\mu$F is chosen so that the discharge time constant (e.g., several seconds) is much longer than the typical impulse duration (e.g., less than 1 millisecond). The voltage across the capacitor is established by internal charging means, such as, for example, a DC—DC converter. In another embodiment, it is established by external charging means. In the later case, the stimulator 64 is capable of generating a finite number of electrical impulses before it has to be recharged by the external charging means.

Actuating means 65 are electrically coupled to processor 63 and preferably embodied by one or more push button switches. Indicator 66 is also electrically coupled to controller 63 and preferably embodied in a single, or multi-segment, LED. Finally, external interface 67 is electrically coupled to controller 63 and preferably embodied as a standard RS-232 serial interface. The controller 63 performs analog-to-digital conversion, senses and controls I/O lines, and processes, analyzes and stores acquired data. The controller 63 is preferably embodied as a single, integrated, low-cost embedded microcontroller. However, in other embodiments, the controller 63 is configured with multiple components, such as, for example, a microprocessor and external components that perform analog-to-digital conversion and other necessary functions.

Figure 4:
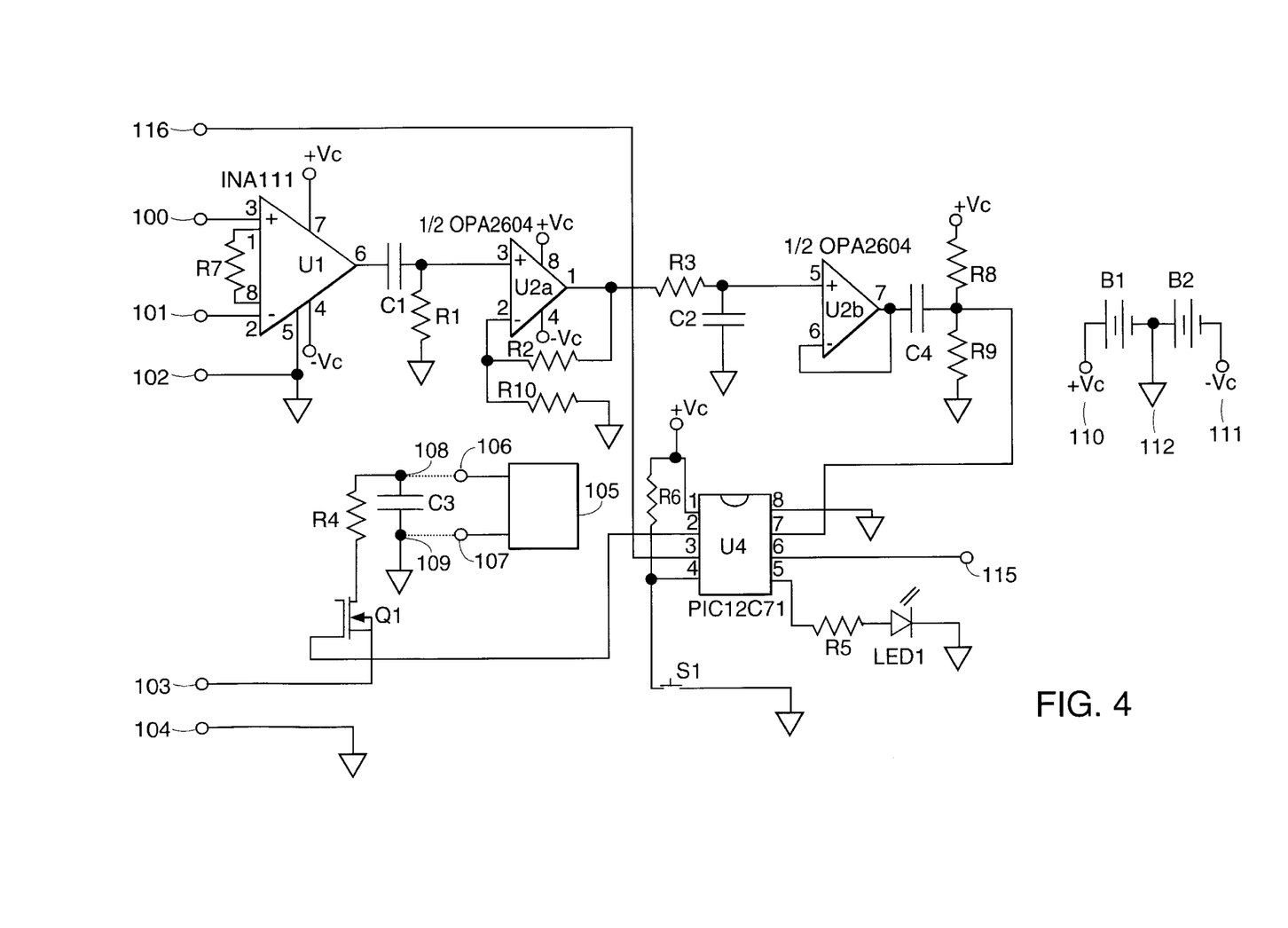
FIG. 4 illustrates electronic circuitry for an embodiment of an apparatus of the invention.

FIG. 4 shows a schematic diagram of the circuitry of one embodiment of the electronic monitor 2 of FIG. 1. The illustrative circuit of FIG. 4 includes a detection sub-circuit, a stimulation sub-circuit and a control and processing sub-circuit. The detection stage is based on amplifier U1, a type INA111 (Burr-Brown, Tucson, Ariz.) instrumentation amplifier. Each of a pair of inputs of amplifier U1, 100 and 101, is electrically coupled to one of the detector sites, 21 and 22, of FIG. 2B. In addition, amplifier U1 has a reference pin 102 at which it receives a reference potential through electrical coupling to reference site 27 of FIG. 2B. U1 is a monolithic instrumentation amplifier and requires one external component, a resistor, R7, to establish its amplification gain, which is preferably a factor of 10. Amplifier U1 is powered by a two sided symmetrical power supply providing +Vc 110 and −Vc 111 (e.g., 6 volts), as well as a ground 112. In a preferred embodiment, +Vc 110, −Vc 111, and the ground 112 are provided by two batteries, B1 and B2, connected in series, as shown in FIG. 4. The output of amplifier U1 is coupled through a high pass filter formed by capacitor C1 and resistor R1 to the input of a non-inverting amplifier formed by operational amplifier U2a. The high pass filter removes any DC offset in the output of amplifier U1. In a preferred embodiment, capacitor C1 and resistor R1 are chosen for a high pass corner frequency of about 2 Hz. The gain of the non-inverting amplifier is established by resistors R2 and R10 and is preferably set to a gain of 500. The output of first operational amplifier U2a is coupled to input of second operational amplifier U2b by a low pass filter formed by resistor R3 and capacitor C2. The low pass filter removes high frequency noise from the signal. In a preferred embodiment, resistor R3 and capacitor C2 are chosen for a low pass corner frequency of about 3 KHz. The second operational amplifier U2b is configured simply as an impedance buffer. The output of amplifier U2b is coupled to an analog-to-digital conversion pin on microcontroller U4 by a DC biasing circuit consisting of capacitor C4, along with resistors R8 and R9. The purpose of the DC biasing circuit is to insure that all signals vary from ground 112 to +Vc110, since the analog-to-digital conversion electronics of microcontroller U4 operate only on positive voltages. The detection stage also has a combination communication and power line 116, for interfacing to a "one-wire" temperature sensor 36 of FIG. 2B, connected to an I/O pin on microcontroller U4.

The stimulation sub-circuit of the apparatus is based on energy storage capacitor C3, which is a high capacitance (e.g., 1 μF or greater) and high voltage (e.g., greater than 100 volts) capacitor. In one embodiment of the apparatus, capacitor C3 is charged to greater than 100 volts by an external charging means 105. Capacitor C3 charging is accomplished by charging means 105, which passes electrical current between terminals 107 and 106, which are temporarily electrically coupled to capacitor C3 terminals 109 and 108 during the charging period. Once capacitor C3 is charged, charging means 105 is removed. Electrical stimulation of nerve and muscle is accomplished by discharging capacitor C3 through leads 103 and 104, which are electrically coupled to stimulation sites, 30 and 31. Control of stimulation duration is provided by a power MOSFET transistor Q1, which gates discharge according to a digital signal from microcontroller U4. Resistor R4 protects transistor Q1 by limiting the current that flows through it.

The control and processing stages of the apparatus are based on microcontroller U4, which is preferably a type PIC12C71 (MicroChip, Chandler, Ariz.) microcontroller. U4 provides processing and storage capabilities, analog-to-digital conversion and input/output control. In addition to the aforementioned connections to detection and stimulation subcircuits, microcontroller U4 detects depression of switch S1, which is connected to an I/O pin and controls light emitting diode LED1, which is also connected to an I/O pin. Resistor R6 limits current into the I/O pin when switch S1 is depressed and resistor R5 limits current through the light-emitting diode LED1. In addition, serial communication 115 to external devices is provided by the remaining available I/O pin. Control and processing algorithms are stored in microcontroller U4 and executed automatically upon application of power. Other electronic circuitry may be used to perform the processes described above and is considered to be within the scope of the invention. One skilled in the art knows how to design electronic circuitry to perform the functions outlined above.

A major object of the present invention is to serve as a detection system for CTS. Conventional detection of CTS is based on an analysis of certain features of the evoked muscle response, typically the distal motor latency (DML). The DML represents the time lag between stimulation of the Median nerve 50 immediately proximal to the wrist crease 9 and arrival of the neurally conducted impulse at the Thenar muscle group 51 after traversing the Carpal Tunnel. One of the most common and consistent indications of CTS is an increase in the DML. Although there is no single definition for the DML, it is generally defined as the amount of time that elapses between the start of the stimulus (i.e., time=0) and the occurrence of a consistent feature on the muscle response.

Figure 5:
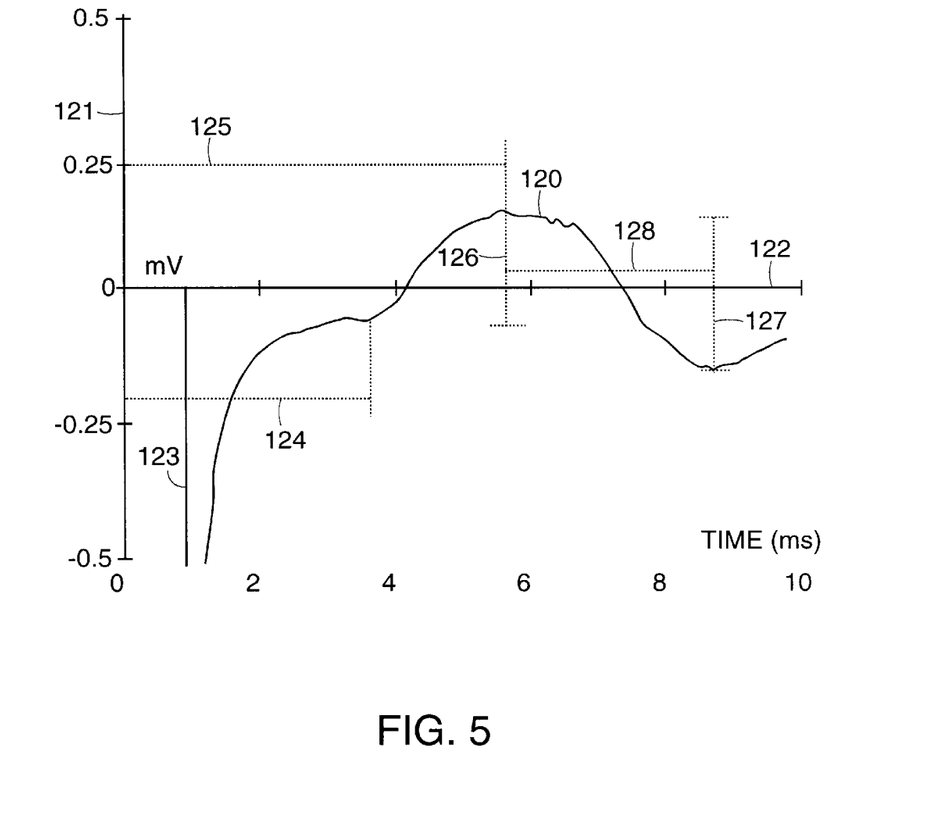
FIG. 5 is a graph showing a muscle response evoked and measured by an apparatus of the invention.

A typical muscle response 120, evoked and acquired using an apparatus of the invention, is shown in FIG. 5. The vertical scale 121 indicates the amplitude of the muscle response in millivolts as measured between detection sites 21 and 22. The horizontal scale 122 indicates the elapsed time from the onset of the stimulation pulse (i.e., stimulus occurred at time=0). The large signal transients 123 that occur in the first 2 milliseconds represent stimulus associated artifacts and are unrelated to activity in the Thenar muscles 51. An evoked muscle response 120 may be characterized by many parameters including, but not limited to, a time to onset 124, a time to peak 125, a peak amplitude 126, a peak to peak amplitude 127 and a peak to peak width 128. In the illustrative example of FIG. 5, the time to onset 124 is about 3.7 milliseconds, and the time to peak 125 is about 5.8 milliseconds.

Because detection of the Thenar muscle 51 response occurs at a significant distance from its physiological site of origin, the intervening tissue acts as a low pass filter. This results in amplitude attenuation and temporal spreading of the detected waveform as compared to measurements taken directly over the Thenar muscles 51. The decrease in amplitude results in a reduction in the signal-to-noise ratio of the detected muscle response 120. The temporal spreading obscures sharp characteristic features of the response 120. Taken together these two low-pass related effects make a consistent and accurate identification of muscle response features, such as the time to onset 124 or the time to peak 125, difficult and highly variable, especially in the presence of various noise sources (e.g., extraneous muscle activity such as would be caused by a muscle twitch in an arm muscle).

Figure 6:
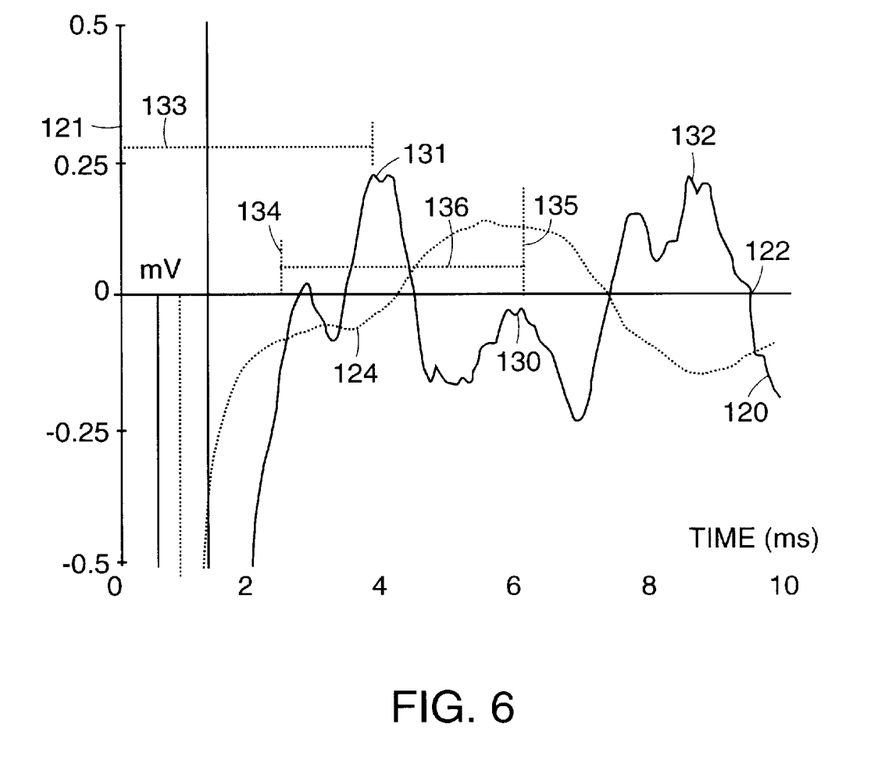
FIG. 6 is a graph showing a second derivative of a muscle response signal evoked and measured by an apparatus of the invention.

In a preferred embodiment, analysis of the muscle response 120 is significantly enhanced by preprocessing it prior to determination of its characteristic features. One such preprocessing step is to take the second derivative of the muscle response 120 as shown in FIG. 6. The advantageous nature of this preprocessing step is evident from the fact that the second derivative 130 (solid line) has a peak 131 near the onset 124 of the muscle response 120. Consequently, it is possible to accurately and consistently obtain a latency estimate 133 by simply detecting the presence of this peak 131. By contrast, a direct estimation of the time to onset 124 from the muscle response 120 requires establishment of an arbitrary voltage threshold which may vary significantly among different individuals.

In a preferred embodiment, the sharp peak 131 in the second derivative 130 of FIG. 6 is obtained by first smoothing the muscle response 120, such as by, for example, convolving it with a normalized Gaussian waveform with a predetermined standard deviation. Subsequently, the first derivative is calculated by estimating the instantaneous slope for each data point in the muscle response 120. The second derivative is then calculated by estimating the instantaneous slope for each data point in the just computed first derivative. In order to conserve dynamic memory resources, the first and second derivatives 130 can be sequentially calculated for small sections of the muscle response 120 and the values discarded if they do not indicate the presence of a peak 131 in the second derivative 130.

Once the peaks 131 in the second derivative 130 have been identified, the largest positive peak within a defined time window 136 is selected. This time window 136 is defined as occurring between two time limits, 134 and 135. In a preferred embodiment, the lower time limit 134 is predetermined and reflects the amount of time required for artifacts 123 associated with the stimulus to decay to an amplitude that is significantly less than the amplitude of the actual signal evoked from the muscle 120. The lower time limit 134 is preferably about 2.5 milliseconds. Other lower time limits may, however, be used. In addition, it is possible to dynamically establish the lower time limit 134 by analyzing the amplitude decay of the stimulus associated artifact 123. The upper time limit 135 is determined dynamically. In a preferred embodiment, the upper time limit 135 is set to reflect the time during which the first derivative of the evoked muscle response 120 is positive. In other words, it reflects the period of time during which the evoked muscle response 120 is increasing. By establishing the upper time limit 135 in this fashion, large peaks 132 in the second derivative of the response 130, which occur in the latter portion of the response, are ignored and, therefore, do not result in incorrect estimates of the latency 133.

Figure 7:
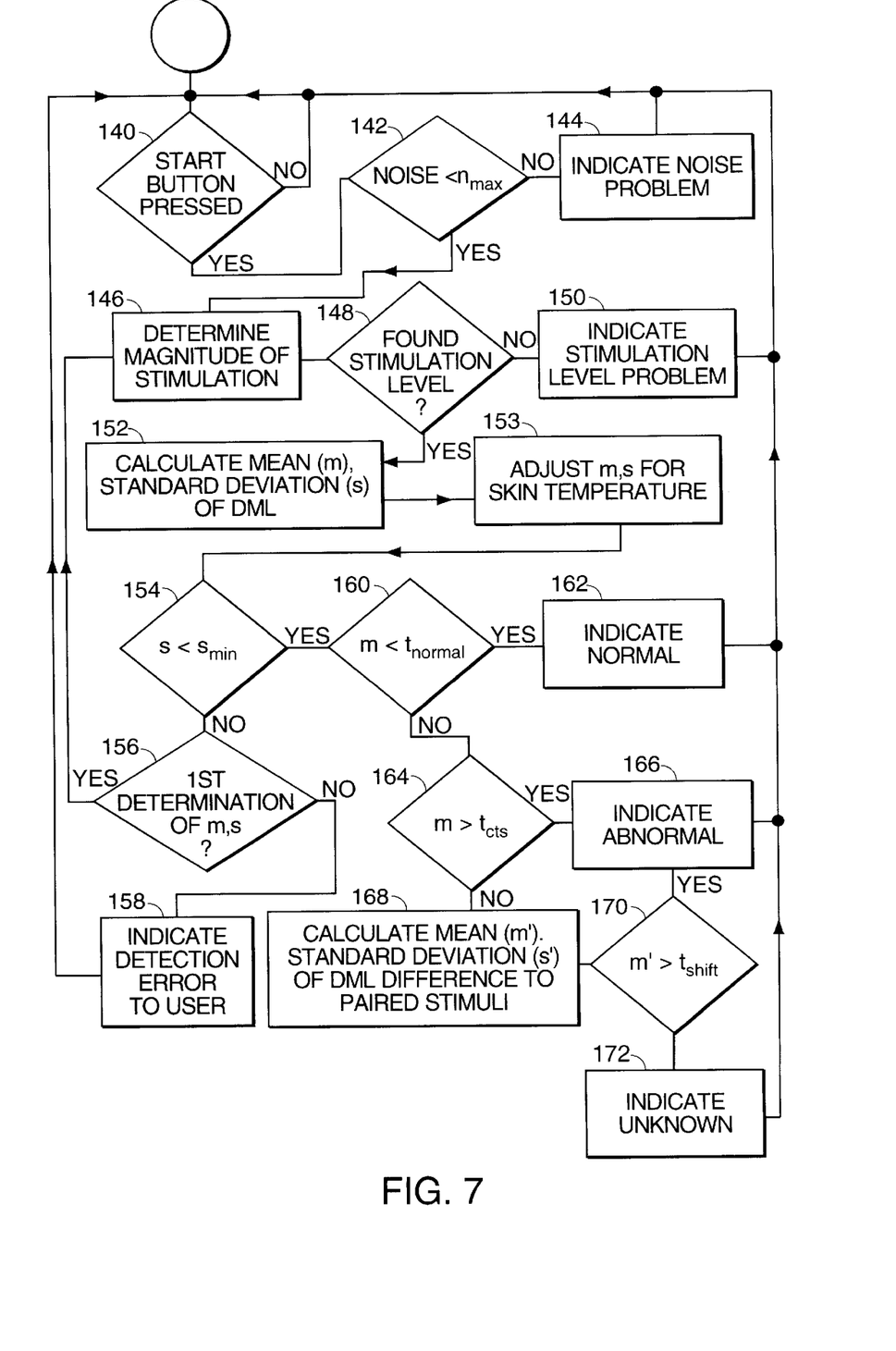
FIG. 7 is flow chart of an embodiment of an algorithm for detecting carpal tunnel syndrome using an apparatus of the invention.

In accordance with a preferred embodiment of the present invention, FIG. 7 shows an illustrative algorithm for detecting CTS using an apparatus of the invention in an entirely automated fashion. The algorithm commences in process step 140 by activation of actuating means 65, such as, for example, by depression of a START switch S1. If the actuation means have been activated, the algorithm continues with process step 142. Otherwise process step 140 is continuously executed until the actuating means are activated. In process step 142, the root-mean-square (RMS) value of the noise is obtained in the absence of any electrical stimulation and compared against a predetermined threshold, $n_{max}$. If the noise RMS is less than $n_{max}$, the algorithm continues with process step 146. However, if the noise RMS is greater than $n_{max}$, the algorithm proceeds to process step 144, in which indicator 66 is used to indicate a problem with the noise level to the user. Subsequently, the algorithm returns to process step 140 and waits for reactivation of the START switch S1.

In process step 146, the magnitude of stimuli to be used in diagnosing CTS is determined. In a preferred process, this parameter is determined automatically without user involvement. This is accomplished by gradually increasing the stimulation duration in predetermined increments (e.g., 25 microseconds) until the evoked muscle response 120 meets one or more predetermined criteria. As an illustrative example, the stimulation duration is increased until the peak of the first derivative of the evoked muscle response 120 exceeds a predetermined threshold (e.g., 0.1 mV/ms). If the proper stimulation duration is obtained, the algorithm proceeds from process step 148 to process step 152. If a proper stimulation magnitude is not obtained, (i.e., predetermined threshold not exceeded) the algorithm proceeds to process step 150, in which indicator 66 is used to indicate a problem with the determination of stimulation magnitude to the user. Subsequently, the algorithm returns to process step 140 and waits for reactivation of the START switch.

Upon determination of the proper stimulation magnitude, the algorithm proceeds with process step 152. In this step, the Median nerve 50 is stimulated at a predetermined rate (e.g., 2 Hz) for a predetermined duration (e.g., 2 seconds). Each Thenar muscle response 120 is analyzed, as previously described, to estimate the distal motor latency (DML) as the first major peak 133 of the second derivative 130 of the muscle response 120. Furthermore, the plurality of DML estimates are combined to obtain a mean DML (m) and a standard deviation (s) about this mean. The algorithm then proceeds to process step 153 in which m and s are adjusted for variations in skin temperature. In particular, the following two adjustment equations are applied:

(A) $m_{corrected} = m_{uncorrected} + k_1 T + k_2$ (B) $S_{corrected} = S_{uncorrected} + k_1 T + k_2$ The corrected mean DML ($m_{corrected}$) and standard deviation ($S_{corrected}$) represent the expected values at room temperature (i.e., 25° C. or 298° K.). The skin temperature, as measured by the temperature sensor 36, is represented by the variable T. The values of constants $k_1$ and $k_2$ are determined by a temperature calibration process. In this process, multiple measurements of the mean DML are obtained at a variety of temperatures spanning the expected range of temperatures over which the invention is normally used (e.g., 25° C. to 40° C.). Subsequently, a linear regression is performed between the temperatures and the mean DML measurements. The constants $k_1$ and $k_2$ are determined directly from the regression coefficients.

The algorithm then continues with process step 154, in which the standard deviation of the DML measurements, s, is compared against a predetermined threshold, $s_{min}$. If s is larger or equal to $s_{min}$, process step 156 is executed. Process step 156 evaluates the number of times m and s have been determined. If these values have been calculated only once, the algorithm returns to process step 146, where determination of the proper stimulation level and all subsequent processing is repeated. If m and s have been determined twice, however, process step 158 is executed, resulting in indication of a diagnostic error to the user through indicator 66. Subsequently, the algorithm returns to process step 140 and waits for reactivation of the START switch S1.

If in process step 154 it is determined that s is less than $s_{min}$, the algorithm proceeds with process step 160. In this step, the mean of the DML estimates, m, is compared against a first predetermined latency threshold, $t_{normal}$. If m is less than $t_{normal}$, the algorithm proceeds to process step 162, in which a normal (i.e., user does not have CTS) test result is indicated to user through indicator 66. Subsequently, the algorithm returns to process step 140 and waits for reactivation of the START switch S1. If m is greater or equal to $t_{normal}$, the algorithm proceeds with process step 164, in which the mean distal motor latency, m, is compared against a second predetermined latency value, $t_{CTS}$. If m is greater than $t_{CTS}$, the algorithm proceeds to process step 166, in which an abnormal (i.e., user has CTS) test result is indicated to user through indicator 66. Subsequently, the algorithm returns to process step 140 and waits for reactivation of the START switch S1.

If neither of the two previous inequalities is true, the algorithm continues with process step 168. In this step, the Median nerve 150 is stimulated by pairs of electrical stimuli spaced apart at a predetermined temporal interval (e.g., 3 milliseconds). For each evoked muscle response 120, the difference between the DML estimated from the first and second stimuli is determined. Furthermore, the plurality of DML difference estimates are combined to obtain a mean DML difference (m') and a standard deviation (s') about this mean. Upon measurement of these two parameters, the algorithm proceeds to process step 170 in which the mean DML difference, m' is compared against a predetermined threshold, $t_{shift}$. If m' is greater than $t_{shift}$, process step 166 is executed, in which an abnormal test result is indicated to the user, as described above. If this inequality does not hold, then an unknown test result is indicated to user in process step 172. Subsequently, the algorithm returns to process step 140 and waits for activation of the START switch S1.

The aforementioned algorithm is intended for illustrative purposes only. Other algorithms may be developed which detect CTS using an apparatus of the invention. For example, parameters other than the DML may be incorporated into the diagnostic algorithm. Illustrative parameters include: waveform features of the evoked muscle response 120, such as, for example, the amplitude and width. Additional illustrative parameters include waveform features of processed forms of the evoked muscle response 120, such as, for example, its derivatives, its Fourier transform, and (other parameters derived from statistical analyses (e.g., principal component analysis). Furthermore, additional parameters are obtained by comparison of any of the above parameters at different stimulation levels.

Although the illustrative algorithms described above pertain to the detection of CTS, the apparatus of the present invention may used to detect other forms of nerve disease and to evaluate neuromuscular blockade. For example, the train-of-four (TOF) protocol, which is commonly used to evaluate the degree of neuromuscular blockade in anesthetized patients, is readily implemented using an apparatus of the invention. In particular, a predetermined number (usually four) of muscle responses 120 are evoked at a predetermined rate (e.g., 2 Hz) and the amplitude 126 of each response determined. Subsequently, the ratio of the amplitude of the last of the plurality of muscle responses to be evoked is divided by the amplitude of the first of the plurality of muscle responses to be evoked. This ratio is recognized as a sensitive indicator of neuromuscular blockade.

The disclosed invention provides a new approach to monitoring neuromuscular physiology. Apparatus and methods are described for the substantially automated and highly efficient measurement of many different parameters of neuromuscular physiology. These indicators may be used to detect Carpal Tunnel Syndrome (CTS) and other peripheral nerve diseases, as well as to monitor neuromuscular blockade caused by pathological, pharmacological and chemical means. The invention possesses the significant advantage that, unlike conventional measurements of nerve conduction across the wrist, the disclosed invention provides for a single integrated neuromuscular electrode that is placed immediately proximal to the wrist (i.e., the wrist crease). This is a very familiar anatomic location and so the placement operation is rapidly and easily undertaken by most adults. Unlike apparatus and methods of the prior art, the disclosed invention does not require placement of multiple sets of electrodes on both sides of the wrist, which is a difficult and error prone procedure for non-experts. An additional advantage of the disclosed invention emerges from the fact that the integrated neuromuscular electrodes may be manufactured as a low-cost, disposable item. Consequently, the possibility of cross-contamination among users of the apparatus is significantly reduced. Furthermore, the low-cost, and ease of use will promote frequent monitoring of neuromuscular disorders, such as CTS, providing the potential benefits of early detection and regular tracking of the disease. Another advantage of the present invention is that the process of evoking, detecting and processing neuromuscular signals is carried out in an entirely automated fashion, without requiring involvement of either the user of the apparatus or trained personnel. A further advantage of the present invention is that the smallest and fewest electrical stimuli consistent with an accurate diagnostic assessment are used. As a result, discomfort to the user is minimized and, in most cases, eliminated entirely.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

What is claimed is:

1. An electrode configuration for assessing a physiological function in an arm and a hand of an individual, comprising:
   (a) a stimulation electrode adapted for applying a stimulus proximal to a wrist of said individual; and
   (b) a detection electrode in a fixed relationship with respect to said stimulation electrode and adapted for detecting proximal to said wrist a myoelectric potential generated by a muscle in said hand of said individual in response to said stimulus, wherein a physiological function is evaluated in response to said stimulus and said myoelectric potential, and wherein said electrodes are sized and shaped for positioning on an anterior aspect of said arm of said individual proximal to said wrist.

2. The electrode configuration of claim 1, further comprising a temperature sensor for detecting a temperature of skin underlying said electrode configuration, wherein said physiological function evaluation is adjustable in response to said skin temperature.

3. The electrode configuration of claim 1, further comprising a reference electrode in electrical communication with said detection electrode and producing a reference potential.

4. The electrode configuration of claim 1, further comprising an electrode housing, wherein said stimulation electrode and said detection electrode are housed in said electrode housing so that a surface of each of said stimulation electrode and said detection electrode contacts skin of said individual underlying said electrode housing when said housing is located on said arm of said individual.

5. The electrode configuration of claim 4, further comprising an attachment mechanism for securing said electrode housing to said arm of said individual, wherein said electrode housing is adapted for placement on said arm of said individual proximal to said wrist.

6. The electrode configuration of claim 4, further comprising a second stimulation electrode, said second stimulation electrode being in a fixed relationship with respect to said stimulation electrode and said detection electrode, and being adapted for producing a stimulus and for applying said stimulus proximal to said wrist of said individual.

7. The electrode configuration of claim 6, wherein said stimulation electrode and said second stimulation electrode are positioned substantially at a center of said electrode housing.

8. The electrode configuration of claim 6, wherein said stimulation electrode and said second stimulation electrode are arranged within said electrode housing such that, when said electrode housing is placed on said anterior aspect of said arm, one of said stimulation electrodes is located immediately proximal to said wrist and the other of said stimulation electrodes is located at a position more proximal from said wrist.

9. The electrode configuration of claim 4, further comprising a second detection electrode, said second detection electrode being in a fixed relationship with respect to said stimulation electrode and said detection electrode and being adapted for detecting proximal to said wrist a myoelectric potential, whereby said myoelectric potential is generated by a muscle in a hand of said individual in response to said stimulus.

10. The electrode configuration of claim 9, wherein said detection electrode and said second detection electrode are arranged within said electrode housing such that, when said electrode housing is placed on said anterior aspect of said arm, one of said detection electrodes is located near a medial side of said arm and the other of said detection electrodes is located near a lateral side of said arm.

11. The electrode configuration of claim 4, wherein said electrode housing comprises a connector adapted for creating an electrical communication between each of said stimulation electrode and said detection electrode with a controller.

12. The electrode configuration of claim 4, wherein said electrode housing is disposable.

* * * * *